(12) United States Patent
Buch et al.

(10) Patent No.: US 11,980,345 B2
(45) Date of Patent: May 14, 2024

(54) CHANNEL DEVICE FOR A SCOPE ASSEMBLY

(71) Applicant: Cipher Surgical Limited, Coventry (GB)

(72) Inventors: Justin Wavell Rosenfelder Buch, Coventry (GB); Hanif Ghanbar, Coventry (GB); Neil Walley, Coventry (GB)

(73) Assignee: CIPHER Surgical Limited, Coventry (GB)

( * ) Notice: Subject to any disclaimer, the term of this patent is extended or adjusted under 35 U.S.C. 154(b) by 391 days.

(21) Appl. No.: 16/319,165

(22) PCT Filed: Jul. 21, 2017

(86) PCT No.: PCT/EP2017/068559
§ 371 (c)(1),
(2) Date: Jan. 18, 2019

(87) PCT Pub. No.: WO2018/015567
PCT Pub. Date: Jan. 25, 2018

(65) Prior Publication Data
US 2019/0274532 A1    Sep. 12, 2019

(30) Foreign Application Priority Data

Jul. 21, 2016    (GB) .................................... 1612647

(51) Int. Cl.
*A61B 1/015*    (2006.01)
*A61B 1/00*    (2006.01)
(Continued)

(52) U.S. Cl.
CPC .......... *A61B 1/015* (2013.01); *A61B 1/00068* (2013.01); *A61B 1/00119* (2013.01);
(Continued)

(58) Field of Classification Search
CPC ............ A61B 1/00066; A61B 1/00068; A61B 1/00119; A61B 1/00128; A61B 1/015;
(Continued)

(56) References Cited

U.S. PATENT DOCUMENTS

| 4,666,430 A | * | 5/1987 | Brown .............. A61M 5/14526 604/249 |
| 4,844,052 A | | 7/1989 | Iwakoshi et al. |

(Continued)

FOREIGN PATENT DOCUMENTS

| CN | 104970753 A | 10/2015 |
| EP | 0051862 | 5/1982 |

(Continued)

OTHER PUBLICATIONS

International Searching Authority, Written Opinion and International Search Report, issued for PCT/EP2017/068559 (15 pages).

(Continued)

*Primary Examiner* — Ryan N Henderson
(74) *Attorney, Agent, or Firm* — Polsinelli PC; Gregory P. Durbin

(57) ABSTRACT

A channel device is disclosed for transporting gas and/or liquid between a control unit and a scope accessory, the channel device comprising a wash line, the wash line comprising: a wash line gas channel; a wash container; a piston; and a wash line wash channel, the wash line gas channel being configured to receive a gas from a wash line gas output of the control unit, the piston being configured to be actuated due to an increase in pressure in the wash line gas channel caused by the received gas to cause a liquid to be expelled from the wash container, the wash line wash channel being configured to transport the expelled liquid to the scope accessory.

7 Claims, 13 Drawing Sheets

(51) Int. Cl.
  *A61B 1/12*      (2006.01)
  *A61B 1/313*     (2006.01)
  *A61M 1/00*      (2006.01)
  *A61M 3/02*      (2006.01)
  *G02B 23/24*     (2006.01)

(52) U.S. Cl.
  CPC ............ *A61B 1/126* (2013.01); *A61B 1/3132* (2013.01); *A61M 1/00* (2013.01); *A61M 1/77* (2021.05); *A61M 3/02* (2013.01); *G02B 23/2484* (2013.01); *A61B 2217/007* (2013.01)

(58) Field of Classification Search
  CPC ........... A61B 1/12; A61B 1/126; A61B 1/127; A61M 5/00; A61M 5/20; A61M 5/204; A61M 5/2046; A61M 5/2053; A61M 5/315; A61M 5/178; A61M 2005/2026
  See application file for complete search history.

(56) References Cited

U.S. PATENT DOCUMENTS

| | | | |
|---|---|---|---|
| 4,998,972 A | 3/1991 | Chin et al. | |
| 5,271,379 A | 12/1993 | Phan et al. | |
| 5,464,008 A | 11/1995 | Kim | |
| 7,475,797 B2* | 1/2009 | Kim .................. | A61M 5/14526 222/387 |
| 7,824,373 B2* | 11/2010 | Kim .................. | A61M 5/2053 604/141 |
| 8,403,834 B2* | 3/2013 | Yamane .................. | A61M 1/81 600/432 |
| 9,839,772 B2* | 12/2017 | Ducharme ............ | A61M 37/00 |
| 9,878,112 B2 | 1/2018 | Torisawa et al. | |
| 10,828,424 B2* | 11/2020 | Anand ................ | A61M 5/3204 |
| 10,994,110 B2* | 5/2021 | Ducharme ............ | A61M 37/00 |
| 11,033,687 B2* | 6/2021 | Nessel ................ | A61M 5/2053 |
| 2005/0070848 A1* | 3/2005 | Kim .................... | A61M 5/2053 604/140 |
| 2005/0222499 A1 | 10/2005 | Banik et al. | |
| 2005/0222534 A1* | 10/2005 | Uesugi .................. | A61B 50/10 600/156 |
| 2006/0058617 A1 | 3/2006 | Sano et al. | |
| 2006/0224144 A1* | 10/2006 | Lee .......................... | A61M 1/67 604/542 |
| 2007/0293821 A1 | 12/2007 | Yribarren et al. | |
| 2008/0188715 A1* | 8/2008 | Fujimoto ............... | A61B 1/125 600/157 |
| 2008/0319166 A1 | 12/2008 | Shen | |
| 2009/0209821 A1* | 8/2009 | Yamane .................. | A61M 1/80 604/218 |
| 2009/0209823 A1* | 8/2009 | Yamane .................. | F04B 33/00 600/158 |
| 2010/0048991 A1* | 2/2010 | Yamane .................. | A61M 1/77 600/106 |
| 2011/0105846 A1 | 5/2011 | Yoshie et al. | |
| 2011/0282197 A1* | 11/2011 | Martz ....................... | A61J 1/10 600/432 |
| 2012/0150101 A1* | 6/2012 | Stearns ................. | A61M 13/00 604/24 |
| 2012/0197084 A1* | 8/2012 | Drach .................... | A61B 1/015 600/123 |
| 2013/0053643 A1 | 2/2013 | Yoshida | |
| 2013/0197471 A1* | 8/2013 | Williams ............... | A61M 5/365 604/247 |
| 2014/0371667 A1 | 12/2014 | Kasuya | |
| 2015/0290404 A1 | 10/2015 | Torisawa et al. | |
| 2016/0243309 A1* | 8/2016 | Cupicha .................. | F16J 1/005 |
| 2016/0249794 A1 | 9/2016 | Suzuki | |
| 2017/0119952 A1* | 5/2017 | Wen .................... | A61M 39/223 |
| 2018/0028761 A1* | 2/2018 | Anand ................. | A61M 5/3204 |
| 2018/0104417 A1* | 4/2018 | Nessel .................. | A61M 5/482 |
| 2018/0214016 A1* | 8/2018 | Thommen ................ | A61B 1/07 |
| 2018/0221597 A1* | 8/2018 | Silver ................. | A61M 13/003 |
| 2019/0274532 A1 | 9/2019 | Buch et al. | |
| 2021/0038809 A1* | 2/2021 | Kim .................. | A61M 5/16809 |
| 2021/0146055 A1* | 5/2021 | Mojarrad .......... | A61M 5/31515 |

FOREIGN PATENT DOCUMENTS

| | | |
|---|---|---|
| EP | 1832226 | 9/2007 |
| EP | 2505123 | 10/2012 |
| EP | 2923631 | 9/2015 |
| EP | 3487381 A2 | 5/2019 |
| GB | 2556616 | 6/2018 |
| GB | 2577974 A | 4/2020 |
| JP | H0595891 A | 4/1993 |
| JP | 2015198821 A | 11/2015 |
| JP | 5885894 B1 | 3/2016 |
| WO | 2015198696 A1 | 12/2015 |
| WO | 2018015567 A2 | 1/2018 |

OTHER PUBLICATIONS

United Kingdom Intellectual Property Office, Combination Search and Examination Report Under Sections 17 and 18 (3), issued for GB 1612647.6 dated Jan. 24, 2017 (6 pages).
Chinese Office Action and English translation, dated Aug. 19, 2022 for corresponding CN Application No. 201780058393.3.
Final Office Action dated Feb. 6, 2023 in co-pending U.S. Appl. No. 17/346,080.
IPA, Notice of Acceptance, issued for co-pending AU Application No. 2017299226, mailed May 18, 2021.
BPO, Office Action, issued for co-pending BR App. No. 112019001051-3, mailed Mar. 1, 2023.
CIPO, Office Action, issued for co-pending CA App. No. 3031464, mailed Jun. 30, 2023.
CIPO, Office Action, issued for co-pending CA App. No. 3031464, mailed Jun. 1, 2022.
CIPO, Office Action, issued for co-pending CA App. No. 3031464, mailed Dec. 15, 2022.
CNIPA, First Office Action, issued for co-pending CN App. No. 201780058393.3, mailed May 25, 2021.
CNIPA, Second Office Action, issued for co-pending CN App. No. 201780058393.3, mailed Jan. 25, 2022.
EPO, Article 94(3) EPC, issued for co-pending EP Application No. 17742746.5, mailed Jun. 2, 2021.
EPO, Rule 115(1) EPC, issued for co-pending EP Application No. 17742746.5, mailed May 17, 2023.
EPO, Article 94(3) EPC, issued for co-pending EP Application No. 17742746.5, mailed Dec. 18, 2019.
EPO, Article 94(3) EPC, issued for co-pending EP Application No. 17742746.5, mailed Sep. 2, 2020.
IPI, Examination Report, issued for co-pending IN Application No. 201917004660, mailed Jul. 27, 2021.
International Searching Authority, International Preliminary Report on Patentability, issued for International Application No. PCT/EP2017/068559, mailed Jan. 31, 2019.
JPO, Notification of Refusal, issued for co-pending JP Application No. 2019-524523, mailed Dec. 22, 2020.
USPTO, Non-Final Office Action, issued for co-pending U.S. Appl. No. 17/346,080, mailed Aug. 31, 2021.
USPTO, Final Office Action, issued for co-pending U.S. Appl. No. 17/346,080, mailed Dec. 6, 2021.
USPTO, Non-Final Office Action, issued for co-pending U.S. Appl. No. 17/346,080, mailed Sep. 21, 2022.
USPTO, Non-Final Office Action, issued for co-pending U.S. Appl. No. 17/346,080, mailed Aug. 23, 2023.
UKIPO, Examination Report, issued for co-pending GB App. No. 1612647.6, mailed Oct. 24, 2018.
UKIPO, Combined Search and Examination Report, issued for co-pending GB App. No. 1911510.4, mailed Feb. 11, 2020.
Brazilian Patent and Trademark Office (INPI), Examination Report, issued for Brazilian Application No. BR112019001051-3, mailed Nov. 21, 2023 (3 Pages).

* cited by examiner

CHANNEL DEVICE FOR A SCOPE ASSEMBLY

This disclosure relates to a system for clearing a surface. In particular, but not exclusively, the surface is a lens or window of an endoscope.

The present disclosure will be discussed in relation to the optics of an endoscope and, in particular, with reference to that of a laparoscope, but by no means is it exclusive to these devices. It can also encompass commercial or other medical optic instrumentation as well as other devices.

Endoscopes are used in minimally invasive surgery (MIS) by surgeons to permit remote visualisation and navigation within a body cavity inside a patient. They act as the eyes of the surgeon whilst a surgical procedure, tissue manipulation or diagnostic investigation is undertaken. One type of endoscope is a laparoscope for abdominal MIS, which is used in specialty areas such as laparoscopic general surgery including upper and lower gastrointestinal surgery, gynecology, obesity surgery (bariatric surgery) and Urology, as well as other surgical sectors utilising a rigid scope or semi rigid scope, including thoracic and pulmonary, ENT, and neurological surgery.

Minimally invasive surgery (MIS), often referred to as "keyhole surgery" as well as Minimum Access Surgery (MAS) is defined as a surgical method using small abdominal skin incisions (or no abdominal skin incisions, in which case a natural orifice is used in conjunction with an internal incision) compared with classic open surgical procedures that require large incisions. In MIS, a special access port called a cannula is inserted into the skin incision through which a miniature camera is introduced into the body and transmits images to a video monitor, thereby allowing the physician to visualise, diagnose and, if necessary, treat a variety of conditions.

MIS is already an integrated part of daily surgical activity in surgical centres around the world. Many procedures are now performed by this "keyhole" approach using an appropriate endoscope, or by reduced open surgery (such as mini-open or laparoscopically assisted procedures or hand assisted laparoscopic surgery or single incision laparoscopic surgery), where the skin incision is reduced compared with only a few years ago. The development of these MIS approaches is rapidly on-going and development of new techniques that will aid patients and society because of reduced complications, patient morbidity and hospital stay compared with the corresponding "old" methods will continue to drive the majority of procedures to MIS.

The endoscope used in laparoscopy is called a laparoscope and is comprised of an elongated, typically cylindrical, shaft containing optical elements such as a camera, lighting provisions such as an optical fibre bundle and other equipment. During laparoscopy procedures, laparoscopes are used to visualise the target anatomy. In laparoscopy, the laparoscope is inserted through a cannula or port, which has been introduced through a small incision, next to the umbilicus (belly button) in the patient to access the abdominal cavity. The abdominal cavity is generally insufflated via this port (although other ports can be used) with medical grade carbon dioxide, or another suitable gas, via an insufflator device in order to expand or distend the abdominal cavity by elevating the abdominal wall and hence creating an operating space or environment. Insufflators for general surgical use within theatres are programmed to activate on and off to maintain and optimise the set pressure within the patient's abdominal cavity.

During a laparoscopic procedure, there are four main requirements for a surgeon or practitioner: continuous operative vision, maintained operative control, safety and time efficiency. The laparoscope or endoscope lens in an MIS procedure is the surgeon's "eyes" and the optics regularly become soiled by peritoneum or other bodily fluid, blood, aerosol fat, tissue particulate, smoke, debris or condensation, all of which impair the surgeon's vision (via an external monitor/screen). These various soiling components are disturbed by various instruments introduced into the abdominal cavity via working ports, such as electro-cautery coagulation devices, laparoscopic scissors, ultrasonic coagulation cutting devices, suction-irrigation devices and many others. Since these instruments are an important part of MIS and laparoscopic procedures, in general, they will remain as the main source of lens contamination. As a result of this contamination, visualisation via the laparoscope optics is regularly diminished and impaired.

Currently, the standard procedure for soil removal and lens cleaning requires the laparoscope to be removed from the patient's abdominal cavity. The offending contamination is removed with a sterile swab, then the laparoscope optics are washed in hot sterile saline, then excess saline is removed with another clean swab and finally the lens is coated with a sterile anionic-surfactant (such as Fog Reduction Elimination Device (F.R.E.D.) or ClearIt™ anti-fog solution). From the moment of diminished visualisation, the scope is removed and an immediate stop in the surgical procedure occurs. During this period, the patient can be exposed to increased risk since the surgeon can no longer see the operating field. In other words, the surgeon is blinded. Further to this, there is an interruption in surgeon workflow and an increase in surgical theatre time and time of the patient being under general anaesthesia. Removal of the laparoscope for cleaning can occur up to 5-10 times per hour and the process of cleaning typically takes 40-60 seconds, thereby adding 3-10 minutes per hour of operative time and patient time under general anaesthesia. However, more importantly, the surgeon's workflow and concentration is broken, compromising patient safety. The safety issues associated with removing the laparoscope for cleaning are well understood and attempts have been made to solve this problem in the past. These attempts have been inadequate at solving the myriad of problems associated with cleaning the lens in-situ.

An invention is set out in the independent claims. Optional features are set out in the dependent claims.

In an aspect there is provided a channel device for transporting gas and/or liquid between a control unit and a scope accessory, the channel device comprising a wash line, the wash line comprising: a wash line gas channel; a wash container; a piston; and a wash line wash channel, the wash line gas channel being configured to receive a gas from a wash line gas output of the control unit, the piston being configured to be actuated due to an increase in pressure in the wash line gas channel caused by the received gas to cause a liquid to be expelled from the wash container, the wash line wash channel being configured to transport the expelled liquid to the scope accessory.

In some embodiments, the wash line comprises a valve configured to enable the liquid in the wash container to be replenished while the wash container remains in position in the wash line. In some embodiments, the wash container is replaceable in the wash line with a replacement wash container to provide a replacement supply of the liquid.

In some embodiments, the channel device comprises a gas line, the gas line comprising a gas line channel configured to receive a gas from a gas line gas output of the control unit, and to transport the received gas to the scope accessory.

In some embodiments, the channel device comprises an identifier configured to enable the control unit to identify the channel device while the channel device is connected to the control unit.

In an aspect there is provided an assembly comprising the channel device and the scope accessory. In some embodiments, the scope accessory is arranged to guide the gas and/or liquid across an optical surface of a scope, In some embodiments, the scope accessory comprises a conduit configured to transport the gas and/or the liquid from an input end of the scope accessory to an output end of the scope accessory. In some embodiments, the scope accessory is configured to removably receive the scope.

In an aspect there is provided an assembly comprising the channel device, the scope accessory and the scope.

In an aspect there is provided a control unit for controlling a flow of gas and/or liquid across an optical surface of a scope via a channel device and a scope accessory, the control unit comprising: a gas inlet for receiving a supply of gas; a gas line gas output for outputting a first output of gas from the supply of gas to cause the flow of gas across the optical surface; and a wash line gas output for outputting a second output of gas from the supply of gas to cause the flow of liquid across the optical surface.

In some embodiments, the control unit comprises a gas line binary valve switchable between a closed position and a fully open position to provide binary control of gas flow through the gas line gas output. In some embodiments, the control unit comprises a gas line variable valve switchable between a plurality of positions including at least a closed position, a partially open position and a fully open position to provide variable control of gas flow through the gas line gas output. In some embodiments, the control unit comprises a wash line binary valve switchable between a closed position and a fully open position to provide binary control of gas flow through the wash line gas output. In some embodiments, the control unit comprises a wash line variable valve switchable between a plurality of positions including at least a closed position, a partially open position and a fully open position to provide variable control of gas flow through the wash line gas output.

In some embodiments, the control unit comprises an identification sensor configured to detect the presence of the channel device and identify a property of the channel device.

In some embodiments, the control unit is configured to implement at least one predetermined flow routine comprising a predetermined gas flow routine and a predetermined liquid flow routine.

In some embodiments, a first routine of the at least one predetermined flow routine comprises a first period of time and a second period of time after the first period of time, the average gas flow rate through the gas line gas output being higher during the first period of time than during the second period of time. In some embodiments, in the first routine of the at least one predetermined flow routine, the gas flow rate through the wash line gas output is zero during the first period of time and the second period of time.

In some embodiments, a second routine of the at least one predetermined flow routine comprises at least one pulse of gas flow through the gas line gas output. In some embodiments, the second routine of the at least one predetermined flow routine comprises at least one pulse of gas flow through the gas line wash output. The first and second routines may exist independently without the respective other routine.

In some embodiments, the control unit is configured to initiate at least one of the first output of gas and the second output of gas in response to a determination that the optical surface of the scope has entered an environment in which condensation of the optical surface is expected to occur. In some embodiments, the environment is a cavity. In some embodiments, the control unit is configured to, in response to the determination that the optical surface of the scope has entered an environment in which condensation of the optical surface is expected to occur, use an initial measurement of the pressure of the cavity 18 to determine a maximum pressure threshold for the cavity.

In some embodiments, the control unit is configured to be remotely operated.

In an aspect there is provided an assembly comprising the control unit and the channel device. In an aspect there is provided an assembly comprising the control unit, the channel device and the scope accessory. In an aspect there is provided an assembly comprising the control unit, the channel device, the scope accessory and the scope.

In an aspect there is provided a wash container and a piston for use with a wash line, the wash line comprising a wash line gas channel and a wash line wash channel, the wash line gas channel being configured to receive a gas from a wash line gas output of a control unit, the wash container and the piston being removably insertable into the wash line such that, while the wash container and the piston are situated in the wash line, the piston is configured to be actuated due to an increase in pressure in the wash line gas channel caused by the received gas to cause a liquid to be expelled from the wash container, the wash line wash channel being configured to transport the expelled liquid to a scope accessory.

The present system overcomes disadvantages of prior art systems by providing an improvement over scope pretreatments and removal of the scope from the cavity for cleaning. Debris and contamination are cleared by dispensing gas directly to the patient and to the wash container, allowing a carefully designed sequence of pulses to perform an optimum cleaning cycle in a few seconds.

Additionally, the condensation issue, where a scope at room temperature is inserted into the warm, moist environment of the body causing condensation on the lens, is overcome by providing a shaped controlled pulse of gas. This acts as a cleaning pulse followed by flows of gas for a predetermined amount of time which maintains the clarity of vision whilst the scope temperature reaches and exceeds dew point. This removes the need for pre-treatment of the scope prior to use or the removal of the scope during the procedure, which can cause the risks outlined previously.

Specific embodiments are now described with reference to the drawings, in which.

Figure 1:
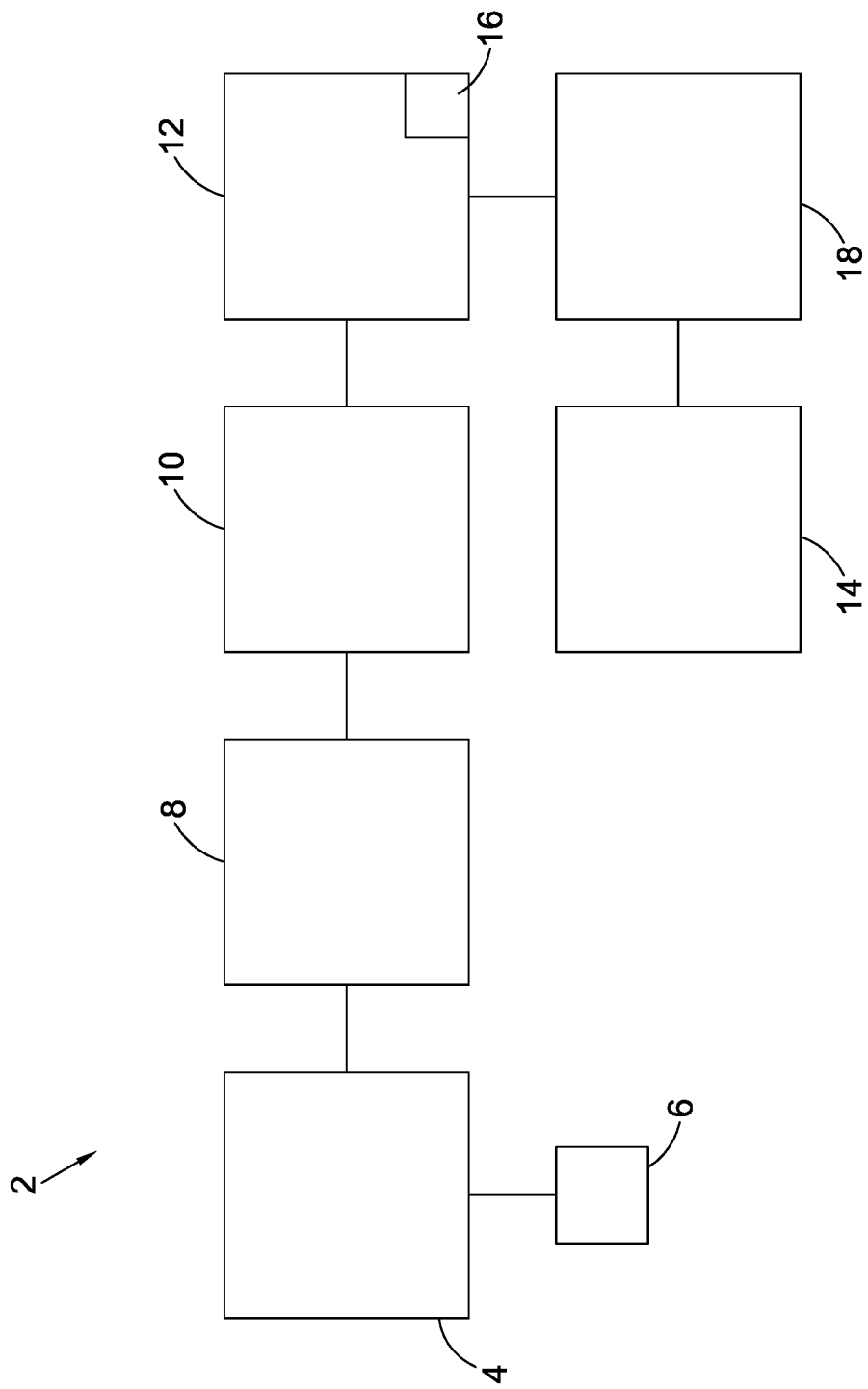
FIG. 1 is a block diagram of an assembly according to an embodiment of the present disclosure.

With reference to FIG. 1, an assembly 2 comprises a control unit 4, an activator 6, a channel device 8, a scope accessory 10, a scope 12 and an insufflator 14. The activator 6 is configured to activate and/or deactivate the control unit 4. The control unit 4 and the channel device 8 are configured to provide a gas and a liquid to the scope accessory 10. The scope accessory 10 is configured to be coupled to the scope 12. The scope accessory 10 is configured to receive the gas and the liquid from the channel device 8. The scope accessory 10 is configured to guide the liquid and the gas to an optical surface 16 of the scope 12 while the scope 12 is coupled to the scope accessory 10. The scope accessory 10 is configured such that the gas and the liquid provided to the optical surface 16 of the scope 12 enhance visibility through the optical surface 16 of the scope 12. In some embodiments, the visibility is enhanced by removing material from the optical surface 16 of the scope 12. In some embodiments, the visibility is enhanced by shielding the optical surface 16 of the scope 12 from material that may otherwise have interacted with the optical surface 16 of the scope 12 to reduce visibility through the optical surface 16 of the scope 12. The insufflator 14 is configured to provide an insufflator gas to create, maintain and/or enlarge a cavity 18. In some embodiments, the cavity 18 is formed inside a human body. The scope 12 is configured to at least partially enter the cavity 18, such that an image of the cavity 18 can be produced from light passing through the optical surface 16 within the cavity 18.

Figure 2:
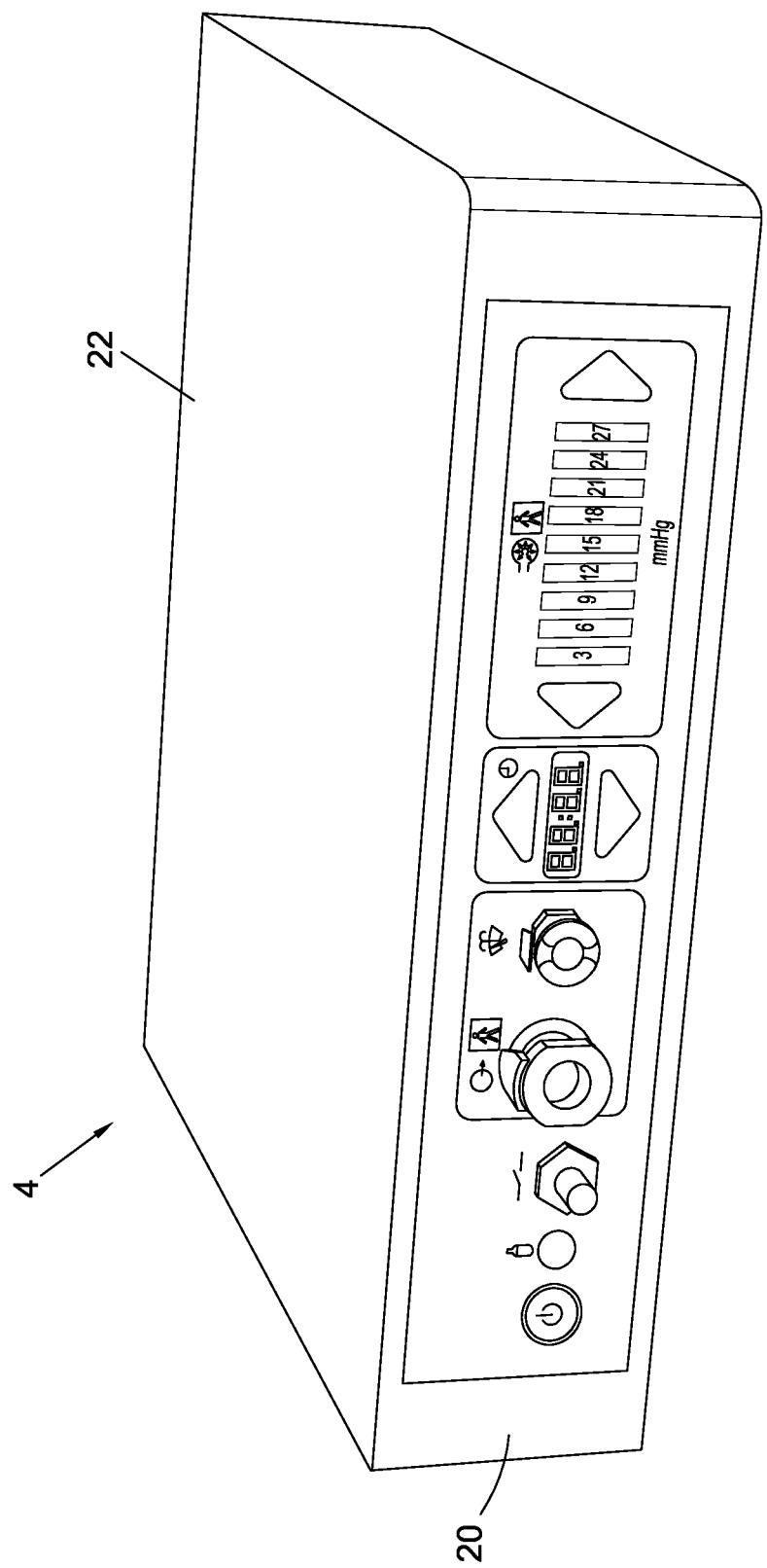
FIG. 2 depicts a control unit of the assembly.

With reference to FIG. 2, the control unit 4 is described. The control unit 4 has a front panel 20 and a rear panel 22. The front panel 20 comprises output sockets and a user interface. The rear panel 22 comprises input sockets.

Figure 3:
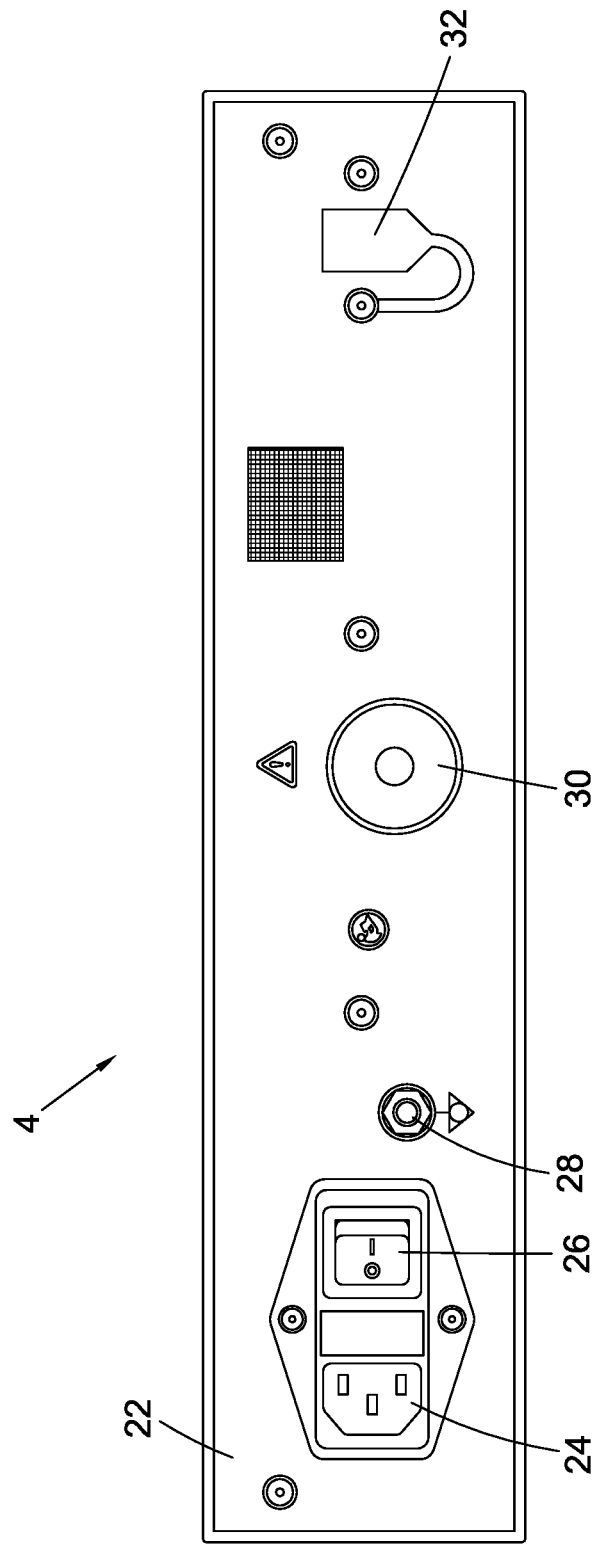
FIG. 3 depicts a rear panel of the control unit.

With reference to FIG. 3, the rear panel 22 comprises a power input 24, a power switch 26, an equipotential bond point 28, a gas inlet 30 and a data transfer port 32. The power input 24 is configured to receive electrical power from a power source to provide electrical power to the control unit 4. The power switch 26 is operable by a user to alternately switch off and on the power supply of the control unit 4 from the power input 24. The equipotential bond point 28 provides a point for equipotential bonding. The equipotential bond point 28 is configured to protect a user from receiving an electric shock from any surfaces of the control unit 4. The equipotential bond point 28 is connectable to a grounding point, such as a common electrical potential point, to ensure that the control unit 4 does not become electrically charged. The gas inlet 30 is configured to receive a supply of gas for use by the control unit 4. The gas inlet 30 is configured to connect to a hose for transmitting the gas to the gas inlet 30. The gas is carbon dioxide. The data transfer port 32 is configured to send and/or receive data to/from an external computer. The data transfer port 32 enables the operational characteristics of the control unit 4 to be (re)configured. The data transfer port 32 is configured to provide recorded usage data of the control unit 4 to the external computer.

The control unit 4 is configured to be remotely operated. The remote operation is carried out by a central control system. The central control system is also configured to control other devices used during a surgical procedure. The control unit 4 is configured to receive control signals from the central control system and operate according to the received control signals. The control unit is configured to receive control signals from the central control system via the data transfer port 32. In some embodiments, the control unit 4 is configured to receive control signals from the central control system via a wireless data connection. The control unit 4 is configured to allow either only a subset of its possible actions or all of its possible actions to be controlled via the central control system. The remote operation enables a user to combine operation of the control unit 4 with operation of other devices used during a surgical procedure.

Figure 4:
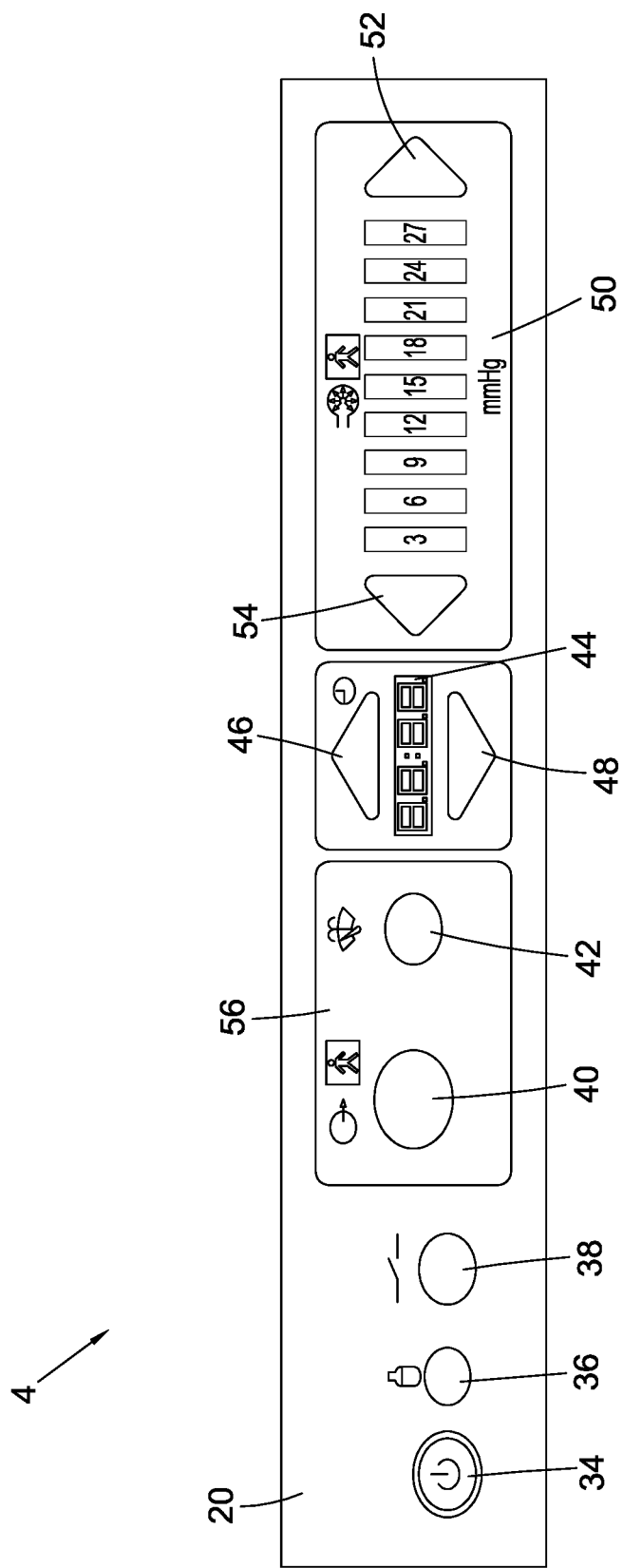
FIG. 4 depicts a front panel of the control unit.

With reference to FIG. 4, the front panel 20 of the control unit 4 comprises a standby button 34, a supply pressure indicator 36, an activator input 38, a gas line gas output 40, a wash line gas output 42, a demist timer display 44, an increase demist timer button 46, a decrease demist timer button 48, a cavity pressure display 50, an increase cavity pressure button 52 and a decrease cavity pressure button 54.

The standby button 34 is operable by a user to alternate between a standby mode and an active mode of the control unit 4. The supply pressure indicator 36 is configured to provide an indication indicative of the pressure of the gas received via the gas inlet 30. The supply pressure indicator 36 is configured to provide the indication in response to a determination by the control unit 4 that the pressure of the gas received via the gas inlet 30 has decreased below a predetermined level. This provides a warning to the user that the supply of gas via the gas inlet 30 will soon run out. The activator input 38 is configured to receive an input from the activator 6. In this embodiment, the activator 6 is a foot switch. The control unit 4 is configured to detect user actuation of the activator 6 via the activator input 38 and take action in response to the detected actuation of the activator 6. The activator 6 is configured to activate the control unit 4 in response to the user actuation of the activator 6.

The gas line gas output 40 and the wash line gas output 42 are configured to output gas received from the gas inlet 30. The control unit 4 is configured to control the rate of gas output through each of the gas line gas output 40 and wash line gas output 42. The gas line gas output 40 and the wash line gas output 42 are configured to removably receive a gas output cover 56. The gas output cover 56 is configured to provide sterilisation protection of sterilised components connected to the gas line gas output 40 and the wash line gas output 42.

The control unit 4 comprises a gas line binary valve. The control unit 4 is configured to switch the gas line binary valve alternately between a closed position and a fully open position, thereby providing binary control of gas flow through the gas line binary valve.

The gas line binary valve is in communication with the gas line gas output 40, such that gas flowing through the gas line binary valve flows through the gas line gas output 40. In this embodiment, the gas line binary valve comprises a solenoid valve. The control unit 4 comprises a gas line variable valve. The control unit 4 is configured to set the gas line variable valve at a desired position of a plurality of positions including at least a closed position, a partially open position and a fully open position. The control unit 4 is thereby able to variably control the rate of gas flow through the gas line variable valve. In this embodiment, the gas line variable valve is a proportional valve. The gas line variable valve is in communication with the gas line gas output 40, such that gas flowing through the gas line valve flows through the gas line gas output 40. The gas line binary valve and the gas line variable valve are operable together and also separately to cause gas to flow through the gas line gas output 40. The gas line binary valve in its open position has a gas flow rate that is equal to or higher than the gas flow rate of the gas line variable valve at its fully open position.

The control unit 4 is configured to use a determined value of the pressure in the cavity 18 to determine the appropriate position of the gas line variable valve to achieve a desired gas flow rate. The value of the pressure in the cavity 18 is determined using a pressure sensor, which measures real pressure whilst no gas is output from the control unit 4, and a flow sensor, which allows calculation of the pressure in the cavity 18 by knowing the resistances to flow at different rates in differing cavity pressures from known internal pressures in the control unit 4. The pressure sensor and the flow sensor are both located in the control unit 4.

The control unit 4 comprises a wash line binary valve and a wash line variable valve, which are configured similarly to the gas line binary valve and the gas line variable valve described above, but with respect to the wash line gas output 42 rather than the gas line gas output 40.

The demist timer display 44 is configured to display a set time, a current time and/or a remaining time for a demist routine (corresponding to one or more of the routines described below). The demist timer display 44 is also configured to display instructions and/or error messages. The increase demist timer button 46 and the decrease demist timer button 48 are configured to be activated by a user to cause the control unit 4 to increase or decrease (respectively) the set/current/remaining time of the demist function.

The cavity pressure display 50 is configured to display the determined pressure of the cavity 18. The cavity pressure display 50 is configured to provide an indication in response to a determination that the pressure in the cavity 18 is above a predetermined safety threshold. The increase cavity pressure button 52 and the decrease cavity pressure button 54 are configured to be activated by the user to cause the control unit 4 to increase or decrease (respectively) the pressure in the cavity 18. The control unit 4 is a separate device from the insufflator 14 and uses a different gas supply. While the cavity 18 is produced primarily by a gas supply from the insufflator 14, gas supplied from the control unit 4 to the cavity 18 also acts to increase pressure in the cavity 18, and a reduction in the amount of gas supplied from the control unit 4 to the cavity 18 helps to avoid an unwanted increase in pressure in the cavity 18.

The control unit 4 comprises an identification sensor configured to detect the presence of a trusted connector connected to the gas line gas output 40 and/or the wash line gas output 42. In this embodiment, the identification sensor is an RFID sensor. The control unit 4 is configured to provide an output from the gas line gas output 40 and/or the wash line gas output 42 in response to a detection by the RFID sensor that a trusted component has been connected. If a non-trusted component is connected, no gas output is provided.

The RFID sensor of the control unit 4 is configured to detect an RFID signal from the channel device 8 indicative of a property of the channel device 8. The control unit 4 may therefore identify a type of channel device 8 that is being used. For example, a different channel device 8 may have a different length of scope accessory 10. The identification of a particular type of channel device 8 enables the control unit 4 to operate in a manner appropriate to the type of channel device 8 that is being used. This arrangement can also be used as a hardware interlock to stop access to software in the control unit 4.

Figure 5:
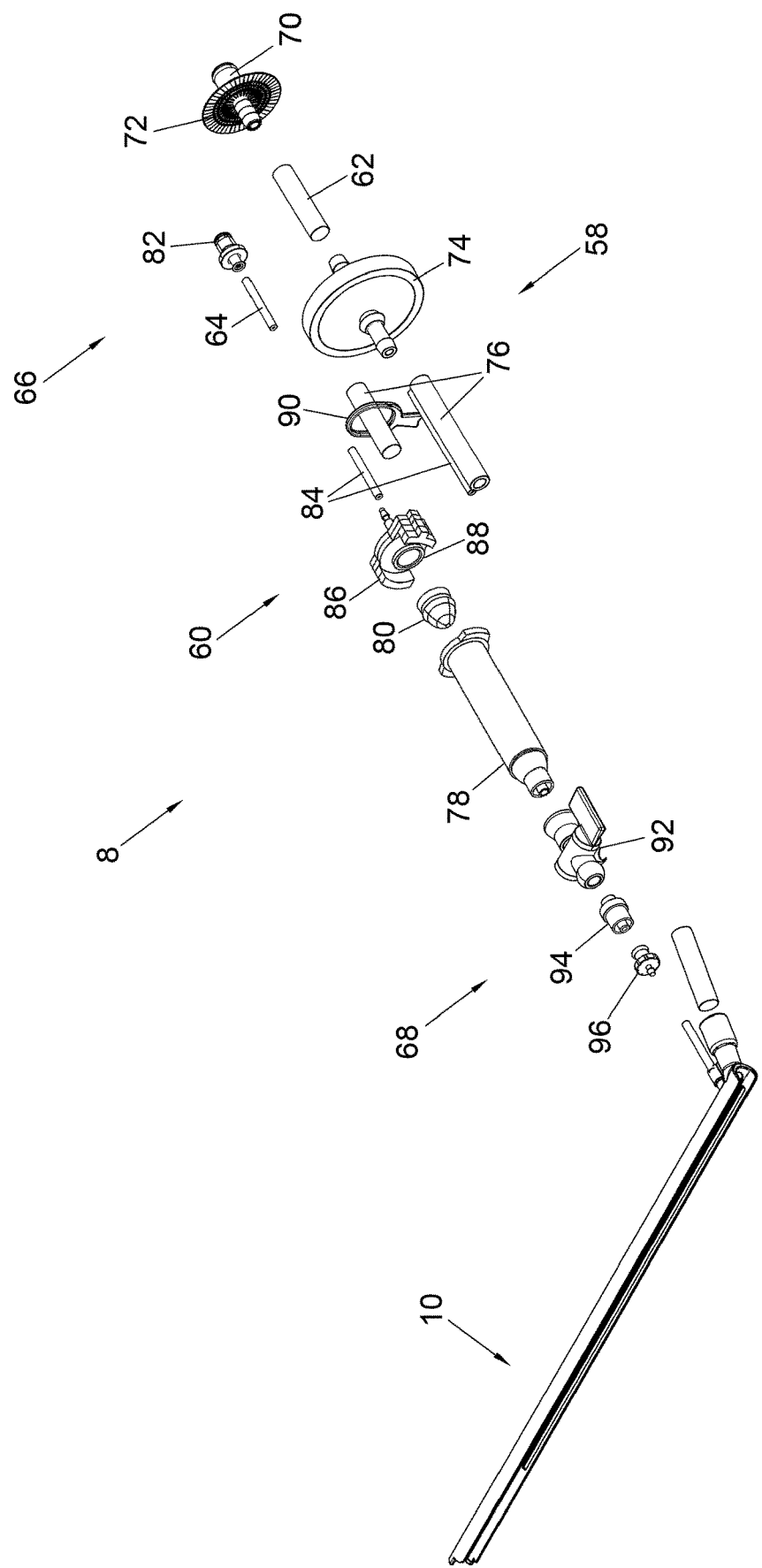
FIG. 5 depicts a scope accessory and a channel device of the assembly.

With reference to FIG. 5, the channel device 8 and the scope accessory 10 are described. The channel device 8 comprises various components which are shown separately in FIG. 5 for illustration. Before use of the channel device 8, these components are integrated together. The channel device 8 comprises a gas line 58 and a wash line 60. Each of the gas line 58 and the wash line 60 is configured to form a channel for gas and/or liquid to travel. The gas line 58 and the wash line 60 are configured to receive a respective supply of gas from the control unit 4. The gas line 58 comprises a gas line channel 62 configured to transport gas between the control unit 4 and the scope accessory 10. The wash line 60 comprises a wash line channel 64 configured to transport gas and/or liquid between the control unit 4 and the scope accessory 10. The gas line channel 62 and the wash line channel 64 each comprise an up-stream end 66 and a down-stream end 68. At the up-stream end 66, the gas line 58 and the wash line 60 are configured to connect to the gas line gas output 40 and the wash line gas output 42 of the control unit 4, respectively. At the down-stream end 68, the gas line 58 and the wash line 60 are configured to connect to the scope accessory 10. In summary, the channel device 8 is configured to provide an output of a gas and/or liquid to the scope accessory 10.

A gas line input connector 70 is configured to connect to the gas line gas output 40 of the control unit 4 (in this embodiment via the gas output cover 56). An RFID transponder 72 is situated in proximity to the gas line input connector 70. The RFID transponder 72 is configured to emit an identification signal. The RFID sensor in the control unit 4 is configured to detect the identification signal. The control unit 4 is configured to activate the gas line gas output 40 and/or the wash line gas output 42 in response to detecting the identification signal. The detection of the identification signal provides an indication to the control unit 4 that the gas line input connector 70 is close to and/or connected to the control unit 4. The control unit 4 is configured to authenticate that the channel device 8 is a trusted device and to enable the channel device 8 to be used with the control unit 4. In this embodiment, the gas line input connector 70 is a hose barb plug. The RFID transponder 72 has a central hole, through which the gas line input connector 70 passes. The RFID transponder 72 is located at a location on the gas line 58 close enough to the up-stream end 66 such that it is able to communicate with the control unit 4 while the gas line input connector 70 is connected to the gas line gas output 40.

Down-stream from the gas line input connector 70, along the gas line channel 62, is a filter 74. The filter 74 is configured to prevent bacteria passing through it in either direction along the gas line 58. The filter 74 comprises a fine mesh. The filter 74 is connected to a gas line tube 76, which is configured to connect the filter 74 to the scope accessory 10.

The wash line 60 is configured to transmit a liquid to the scope accessory 10. In this embodiment, the liquid is a saline solution. The liquid is stored in a wash container 78, which forms part of the wash line 60. Up-stream of the wash container 78, the wash line channel 64 is configured to transport gas from the wash line gas output 42 of the control unit 4 to a piston 80 in the wash container 78. The piston 80 is configured to pressurise the liquid in the wash container 78 such that some of the liquid flows from the wash container 78 towards the scope accessory 10. The piston 80 is actuated by gas pressure from the wash line gas output 42 of the control unit 4.

A wash line input connector 82 is configured to connect the up-stream end 66 of the wash line 60 to the wash line gas output 42 of the control unit 4 (in this embodiment via the gas output cover 56). The wash line input connector 82 is, in this embodiment, a hose barb plug. The wash line input connector 82 is of a smaller cross-sectional area than the gas line input connector 70. The wash line input connector 82 is structured differently from the gas line input connector 70 to ensure that these connectors are not connected to the control unit 4 the wrong way around. Down-stream of the wash line input connector 82, the wash line 60 comprises a wash line tube 84. The wash line tube 84 is twin bonded with the gas line tube 76. The wash line tube 84 has a smaller cross-sectional area than the gas line tube 76. Down-stream of the wash line tube 84, the wash line tube 84 is connected to an adapter head 86 and an "O" ring 88. The adapter head 86 and the "O" ring 88 are configured to support the piston 80 and enable the piston 80 to move within the wash container 78.

A drape clip 90 is configured to be attached to the gas line tube 76. The drape clip 90 is configured to retain the wash line 60 such that the wash container 78 remains proximal to the down-stream end 68 of the channel device 8, close to the scope accessory 10.

The wash container 78 and the piston 80 are configured to be connected to the adapter head 86. The connection is by a quarter turn lock. The wash container 78 is replaceable. Another wash container 78 can replace the wash container 78 in the wash line 60. Within the wash container 78, the piston 80 acts as a barrier. On the up-stream side of the piston 80, gas is present. On the down-stream side of the piston 80, liquid is present (assuming the wash container 78 has not been emptied of liquid). The piston 80 acts as a barrier between the gas and the liquid. The piston 80 therefore prevents the liquid within the wash container 78 from travelling up-stream to the control unit 4, regardless of the orientation and position of the wash container 78.

The wash container 78 is configured to be attached to a valve 92. Liquid expelled from the wash container 78 by the piston 80 enters the valve 92. The valve 92 has an input port for receiving liquid from the wash container 78, an output port for transmitting liquid received from the wash container 78 towards the scope accessory 10, and a refill port for refilling the wash container 78 with liquid. When the refill port is opened, the wash container 78 can be refilled from a syringe applied to the refill port. The refill port is then closed so that the valve 92 is ready for operation. In this embodiment, the valve 92 is a three way stopcock. The output port of the valve 92 is connected to a one way valve 94. The one way valve 94 is configured to allow the liquid to flow down-stream towards the scope accessory 10 and to prevent liquid or gas flowing up-stream into the valve 92. The down-stream side of the one-way valve 94 is connected to an adapter 96, which connects the one-way valve 94 to a final part of the wash line channel 64. The down-stream end 68 of the wash line channel 64 is configured to connect to the scope accessory 10. The part of the wash line channel 64 between the wash line input connector 82 and the wash container 78 is referred to as a wash line gas channel. The part of the wash line channel 64 between the wash container 78 and the scope accessory 10 is referred to as a wash line wash channel.

Figure 6:
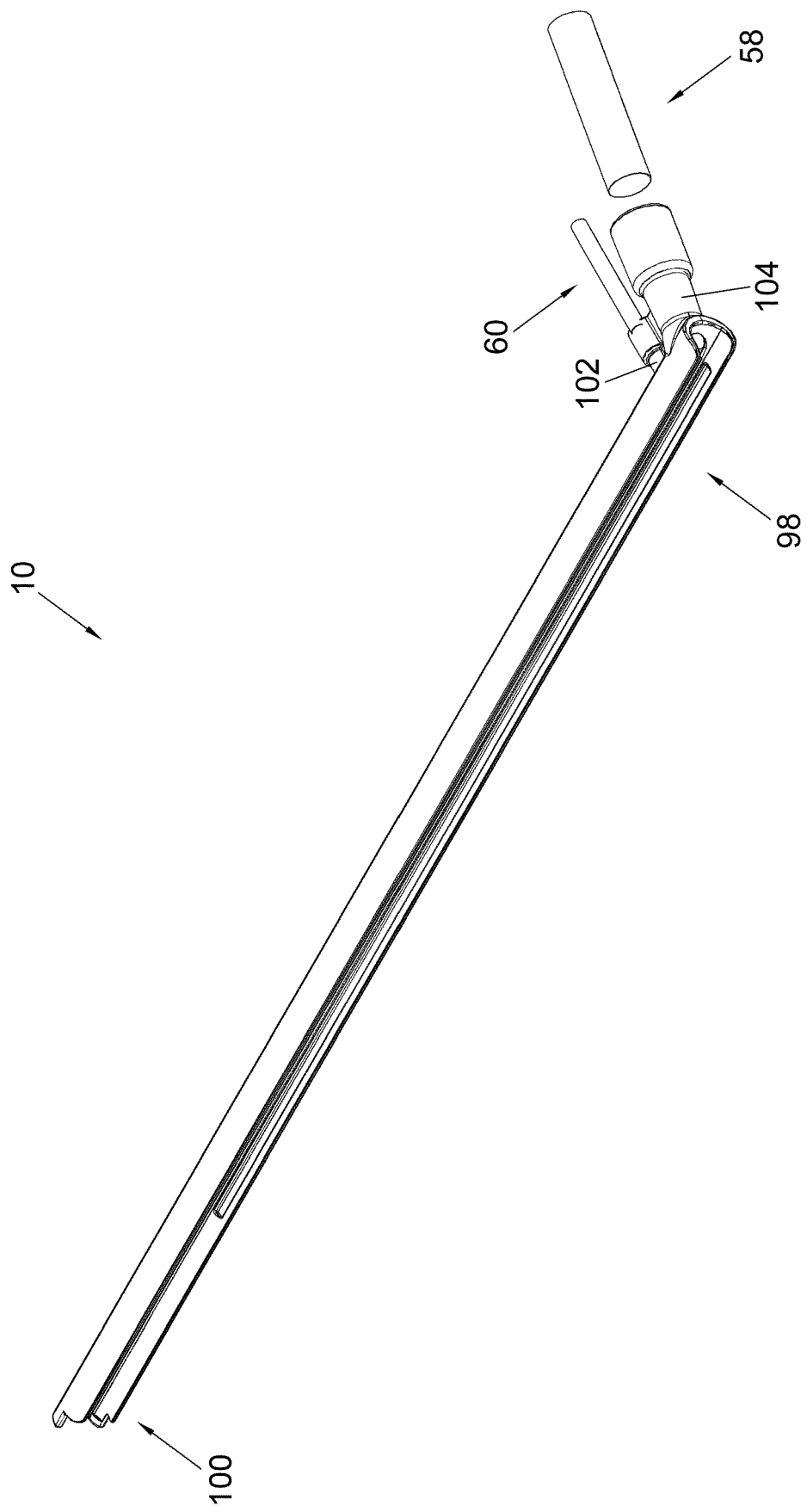
FIG. 6 depicts the scope accessory.

With reference to FIG. 6, the scope accessory 10 comprises an input end 98 and an output end 100. The input end 98 comprises a wash line input 102 and a gas line input 104. The wash line input 102 is configured to receive the liquid from the wash line 60. The gas line input 104 is configured to receive the gas from the gas line 58. The wash line 60 is configured to attach to the wash line input 102 and the gas line 58 is configured to attach to the gas line input 104. In this embodiment, this attaching is achieved by gluing the respective components together, while in other embodiments this is achieved with push fit barbs.

The scope accessory 10 is configured to associate with the scope 12 (not shown). The scope accessory 10 is removably attachable to the scope 12. When the scope accessory 10 and the scope 12 are configured to be ready for operation, a distal end of the scope 12 is associated with the output end 100 of the scope accessory 10, and a proximal end of the scope 12 is associated with the input end 98 of the scope accessory 10. The distal end of the scope 12 comprises the optical surface 16. In this embodiment, the scope 12 is a laparoscope.

At least while the scope accessory 10 is attached to the scope 12, a conduit extends between the input end 98 and the output end 100 of the scope accessory 10. The conduit is defined at least partially by the scope accessory 10. The conduit is configured to receive the liquid from the wash line 60 and the gas from the gas line 58 at the input end 98 of the scope accessory 10. The conduit is configured to transport the received liquid and/or gas to the output end 100 of the scope accessory 10. The output end 100 of the scope accessory 10 is configured to direct the gas and/or liquid from the conduit across the optical surface 16 of the scope 12 (while the scope 12 is attached to the scope accessory 10). In this embodiment, the conduit is partially formed by the scope accessory 10 and partially formed by the scope 12 while it is situated within the scope accessory 10. The scope accessory 10 is configured to grip the scope 12 while the scope 12 is present in the scope accessory 10. The scope accessory 10 has a substantially crescent-shaped cross-section between the input end 98 and the output end 100. The scope accessory 10 is structured differently at the input end 98 and the output end 100, as described above. The longitudinal extent of the scope accessory 10 (between the input end 98 and the output end 100) is substantially longer than the transverse extent of the scope accessory 10. The scope accessory 10 is configured such that, in use, the output end 100 is situated inside the cavity 18, while the input end 98 remains outside the cavity 18.

In this embodiment, the conduit is a single conduit. The conduit is the only conduit between the input end 98 and the output end 100 for the liquid and/or the gas. The liquid and the gas travel along the conduit together when both the liquid and the gas are being provided from the wash line 60 and the gas line 58, respectively. If only one of these is being provided, only the provided liquid or gas travels along the conduit.

When ready for use, the channel device 8 and the scope accessory 10 are provided as an integrated device. The channel device 8 and the scope accessory 10 are provided in a sterilised condition ready for use. If the wash container 78 does not already contain a sufficient supply of liquid, liquid is applied to the wash container 78 via the valve 92, or a filled wash container 78 is inserted as described above. In order to use the assembly 2, the channel device 8 is connected to the control unit 4 by connecting the gas line 58 and the wash line 60 to the gas line gas output 40 and the wash line gas output 42, respectively, of the control unit 4. Before the scope 12 and scope accessory 10 are introduced into the cavity 18, a first user actuation of the activator 6 triggers a prime and purge sequence. In the prime and purge sequence, gas is output by the control unit 4 such that the wash line 60 between the wash container 78 and the scope accessory 10 is filled with liquid from the wash container 78, and air in the gas line 58 is replaced with gas from the control unit 4. After this, the scope 12 and the scope accessory 10 are ready to be introduced into the cavity 18. The scope 12 is paired with the scope accessory 10 and the combination of the scope 12 and the scope accessory 10 is introduced into the cavity 18. The control unit 4 is switched on (this may take place earlier). In response to a second user actuation of the activator 6, the control unit 4 proceeds to transmit gas through one or both of the gas line gas output 40 and the wash line gas output 42 in order to cause the liquid and/or the gas to enter the conduit via the gas line 58 and the wash line 60, respectively, and be applied to the optical surface 16.

The control unit 4 is configured to separately adjust the level of gas output through the gas line gas output 40 and the wash line gas output 42. As a result of this, the control unit 4 is able to determine the flow rate of the liquid and the gas along the conduit of the scope accessory 10 and therefore across the optical surface 16 of the scope 12. The control unit 4 has a plurality of pre-programmed flow routines. In each routine, a predetermined liquid flow routine takes place simultaneously with a predetermined gas flow routine. The predetermined liquid flow routine may be different from the predetermined gas flow routine. Each of these routines lasts for at least a period of time in which the liquid and gas flow rates are varied in a predetermined manner.

Various flow routines will now be described. These flow routines are initiated by the user using the activator 6 or using the control unit 4. Each regime operates for a predetermined period of time unless interrupted part-way through the duration of the regime by the user interacting with the control unit 4 and/or the activator 6. The flow routines are in general carried out during a procedure in which the output end 100 of the scope accessory 10, attached to the scope 12, is in the cavity 18.

Figure 7:
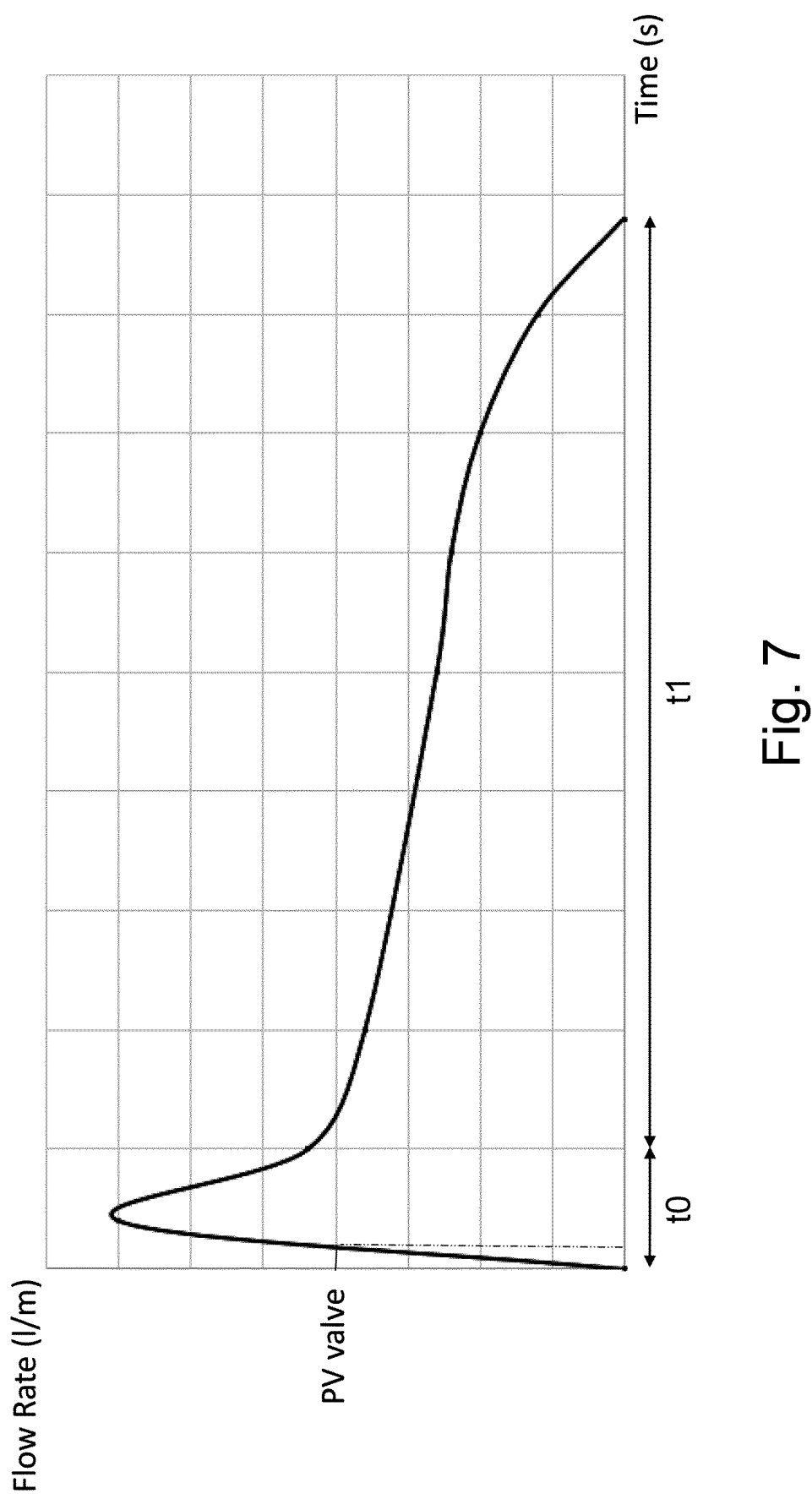
FIG. 7 is a graph of a first condensation avoidance flow routine.

With reference to FIG. 7, a first condensation avoidance flow routine is described. The first condensation avoidance flow routine comprises a flow of gas only. Liquid flow does not form part of the first condensation avoidance flow routine, i.e. the liquid flow is zero throughout. FIG. 7 depicts a graph showing flow rate against time for the gas. The routine is initiated at time t=0 and runs for a predetermined period of time. Upon initiation of the routine, the gas flow rate is increased from zero to a maximum level of the routine. This increase takes place in a minimal amount of time. An initial time period t0 is characterised by a high flow rate. A second time period t1 is characterised by a lower flow rate. During the first time period t0, the flow rate is increased to a maximum level and subsequently decreases to an intermediate level. During the second time period t1, the flow rate decreases gradually from the intermediate level to zero.

The first condensation avoidance flow routine is particularly useful upon entry of the output end 100 of the scope accessory 10 and the distal end of the scope 12 into the cavity 18 at the beginning of a procedure. Typically, the temperature within the cavity 18 is higher than the temperature outside the cavity 18, and the humidity is higher inside the cavity 18 than the humidity outside the cavity 18. In typical operating conditions, the temperature outside the cavity 18 is a room temperature of around 20° C., and the temperature within the cavity 18 is human body temperature of 37° C. In typical conditions, the humidity inside the cavity 18 is in the region of 80% to 100%.

It has been established by the inventors that the introduction of the scope 12 and scope accessory 10 into the cavity 18 from outside the cavity 18 is a situation in which there is a strong likelihood of condensation forming on the optical surface 16 of the scope 12. This condensation reduces visibility through the optical surface 16 during the procedure. The increase in temperature and humidity causes condensation to form on the scope 12, as the scope 12 is initially at a lower temperature than its surroundings.

The first condensation avoidance flow routine is configured to last a length of time corresponding to the length of time that the optical surface 16 of the scope 12 will take to warm to a temperature sufficiently close to the temperature of its surroundings. After the scope 12 has warmed to this temperature, condensation will no longer form. This is also the case because the optical surface 16 will have reached a temperature higher than the dew point.

During the second time period t1, the gradual decreasing of the flow rate corresponds to the increase in temperature of the optical surface 16, and the corresponding decrease in the rate of formation of condensation. In other embodiments, the flow rate during the second time period t1 is constant or substantially constant until the end of this period, when it reduces to zero. A gradually decreasing flow rate reduces the overall gas consumption.

The initial spike in the gas flow rate during the first time period t0 rapidly clears any already-present condensation from the optical surface 16. In the event that the optical surface 16 has been within the cavity 18 for a period of time before the routine is implemented, it is likely that there will be a high level of condensation on the optical surface 16 at the beginning of the routine. The initial high flow rate therefore acts to remove the relatively high amount of condensation in a relatively short period of time. Following the initial removal of the condensation due to the high flow rate, a lower flow rate is required after this to maintain the absence of condensation from the optical surface 16.

In this embodiment, the gas flow during the first time period t0 uses the gas line binary valve. The flow during the second time period t2 uses the gas line variable valve.

Figure 8:
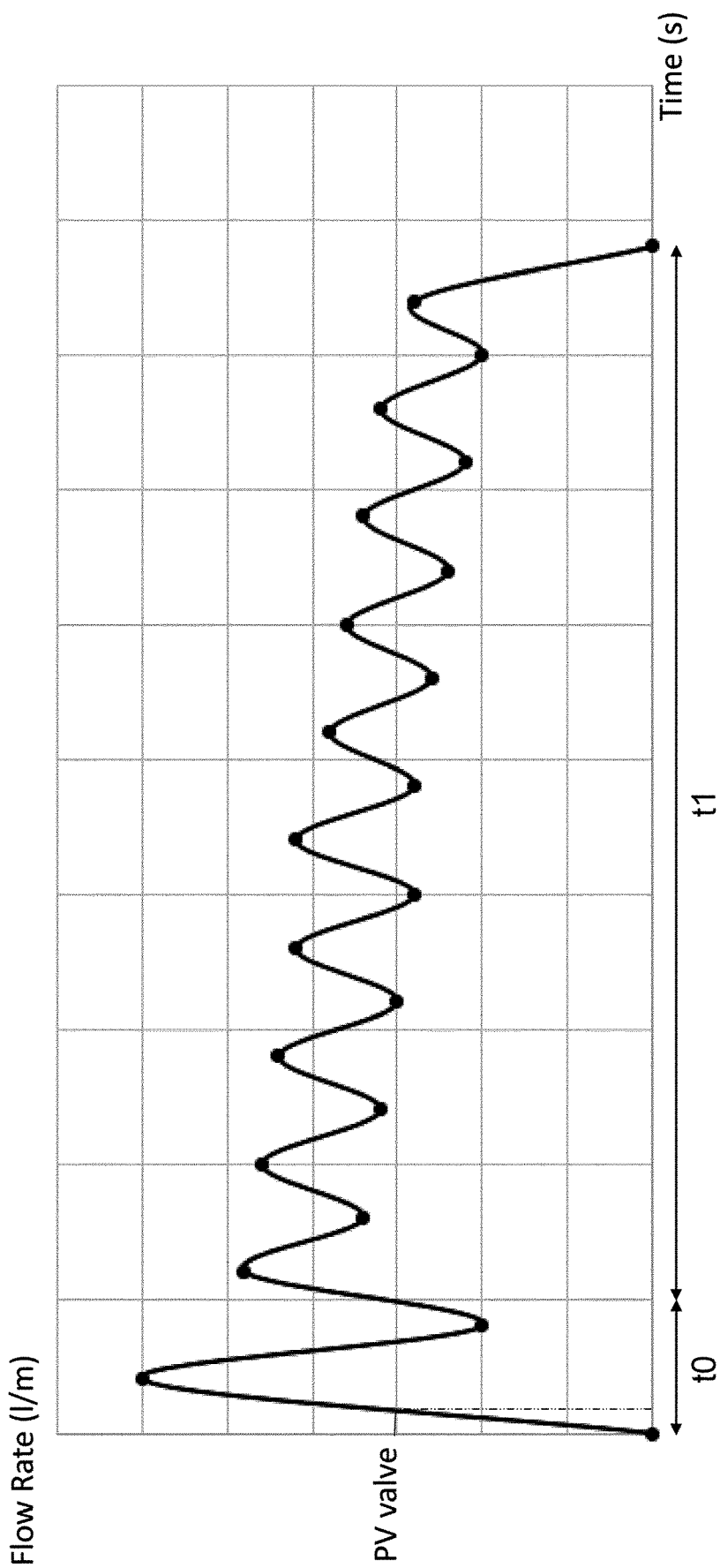
FIG. 8 is a graph of a second condensation avoidance flow routine.

With reference to FIG. 8, a second condensation avoidance flow routine is described. The second condensation avoidance flow routine is similar to the first condensation avoidance flow routine. The main difference between the two routines is that the second condensation routine avoidance flow routine has a sinusoidal variation throughout at least the second time period t1. Each cycle of the sinusoidal variation has a duration of the same order of magnitude, or substantially the same as, the first time period t0. The result of this is that the first time period t0 comprises a substantial increase in flow rate to a maximum level, followed by a decrease in flow rate to a level lower than the intermediate level of the first condensation avoidance flow routine. The flow rate then increases to a level higher than the intermediate level of the first condensation avoidance flow routine. Subsequently, during the second time period t1, the flow rate fluctuates sinusoidally with a gradually decreasing trend until the flow rate is decreased to zero near the end of the second time period t1. The sinusoidally varying flow rate provides additional bursts of gas flow that assist in removing condensation from the optical surface 16.

In this embodiment, the gas flow uses the gas line variable valve only.

Figure 9:
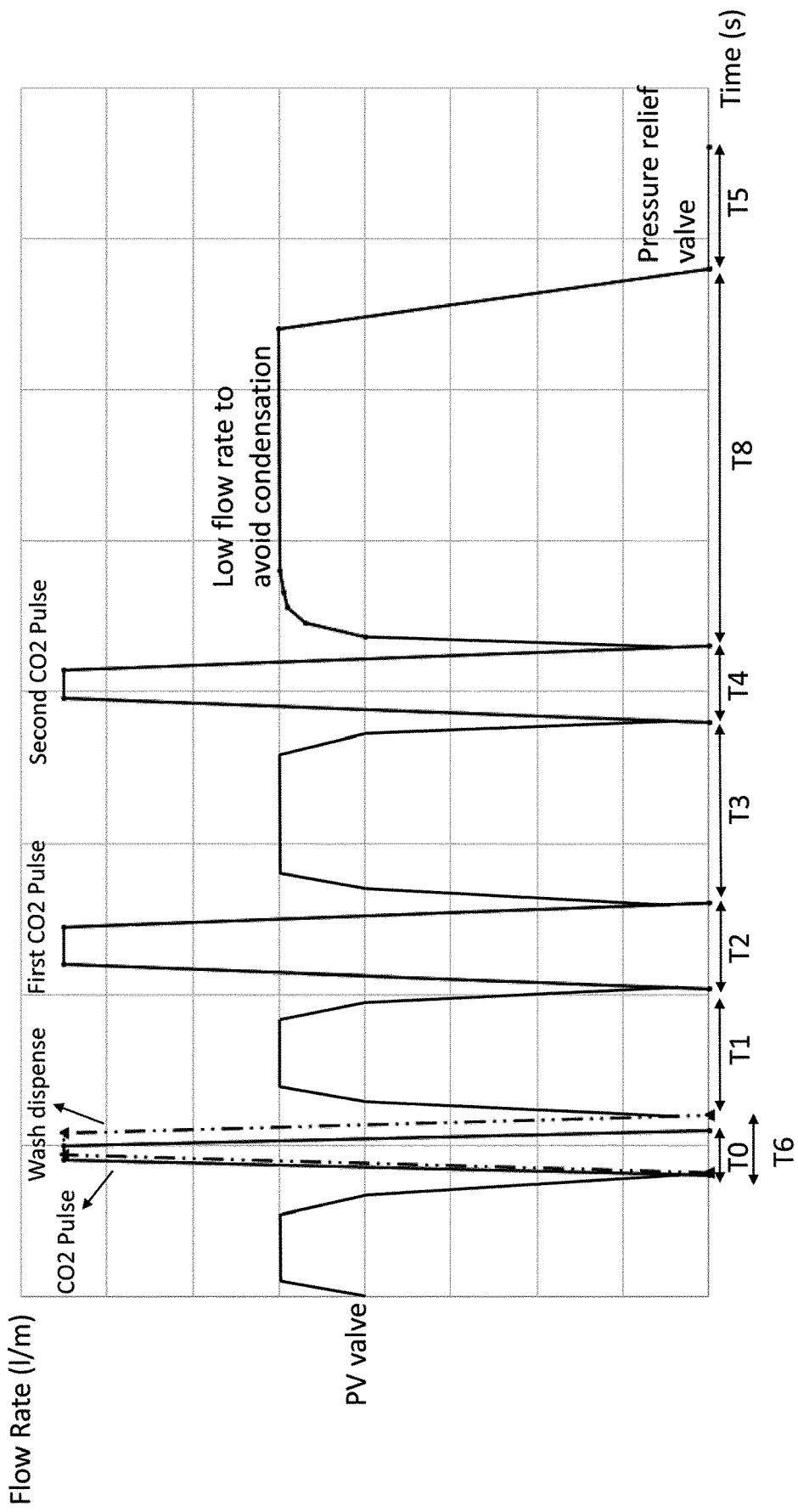
FIG. 9 is a graph of a first gas and liquid flow routine.

With reference to FIG. 9, a first gas and liquid flow routine is described. A first time period T0 is characterised by a high flow rate of both gas and liquid. The flow rates of gas and liquid increase rapidly from zero at the beginning of the first time period T0 and remain at a maximum level until decreasing rapidly to zero at the end of the first time period T0. After the first time period T0, the liquid flow rate remains at zero for the rest of the routine. A second time period T1 is characterised by an intermediate flow rate that is lower than the high flow rate. The flow rate of gas increases from zero at the beginning of the second time period T1 and remains at the intermediate level until decreasing to zero at the end of the second time period T1.

A third time period T2 is characterised by a high flow rate of gas. The gas flow in the third time period T2 corresponds to the gas flow in the first time period T0. A fourth time period T3 corresponds to the second time period T1. A fifth time period T4 corresponds to the third time period T2. A sixth time period T8 corresponds to the fourth time period T3. A seventh time period T5 has a zero flow rate of gas and liquid. In some embodiments, each of the time periods have different durations, while otherwise corresponding as described above. In some embodiments, the routine is configured to be repeated one or more times in succession.

In this embodiment, the high flow rate periods involve the use of the gas line binary valve and/or the wash line binary valve (and not the gas line variable valve and the wash line variable valve). The intermediate flow rate periods involve the use of the gas line variable valve only.

It has been established by the inventors that the first gas and liquid flow routine provides advantages when used during a surgical procedure. The initial high flow of gas and liquid helps to clear the optical surface 16 of any material and/or condensation. The subsequent high flow periods of gas also achieve this while saving liquid. The periods of intermediate gas flow help to avoid condensation.

Figure 10:
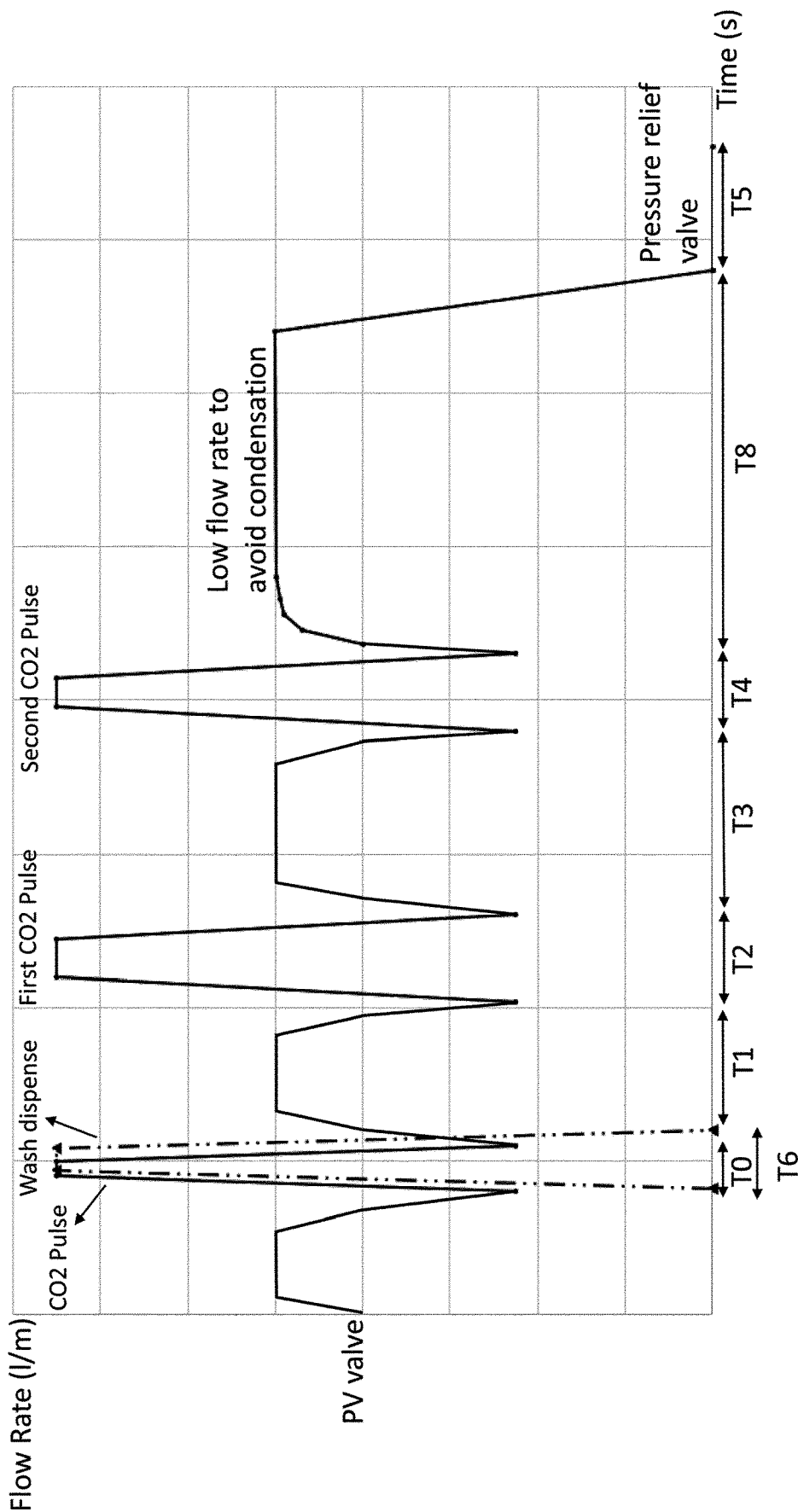
FIG. 10 is a graph of a second gas and liquid flow routine.

With reference to FIG. 10, a second gas and liquid flow routine is described. The second condensation avoidance flow routine is similar to the first condensation avoidance flow routine. The main difference between the two routines is that rather than the flow rates decreasing to zero as in the first gas and liquid flow routine, the flow rates decrease to a non-zero level in the second gas and liquid flow routine. However, at the end of the routine, the flow rate decreases to zero as in the first gas and liquid flow routine. Another difference is that, in the second gas and liquid flow routine, all of the gas flow is via the gas line variable valve only.

Figure 11:
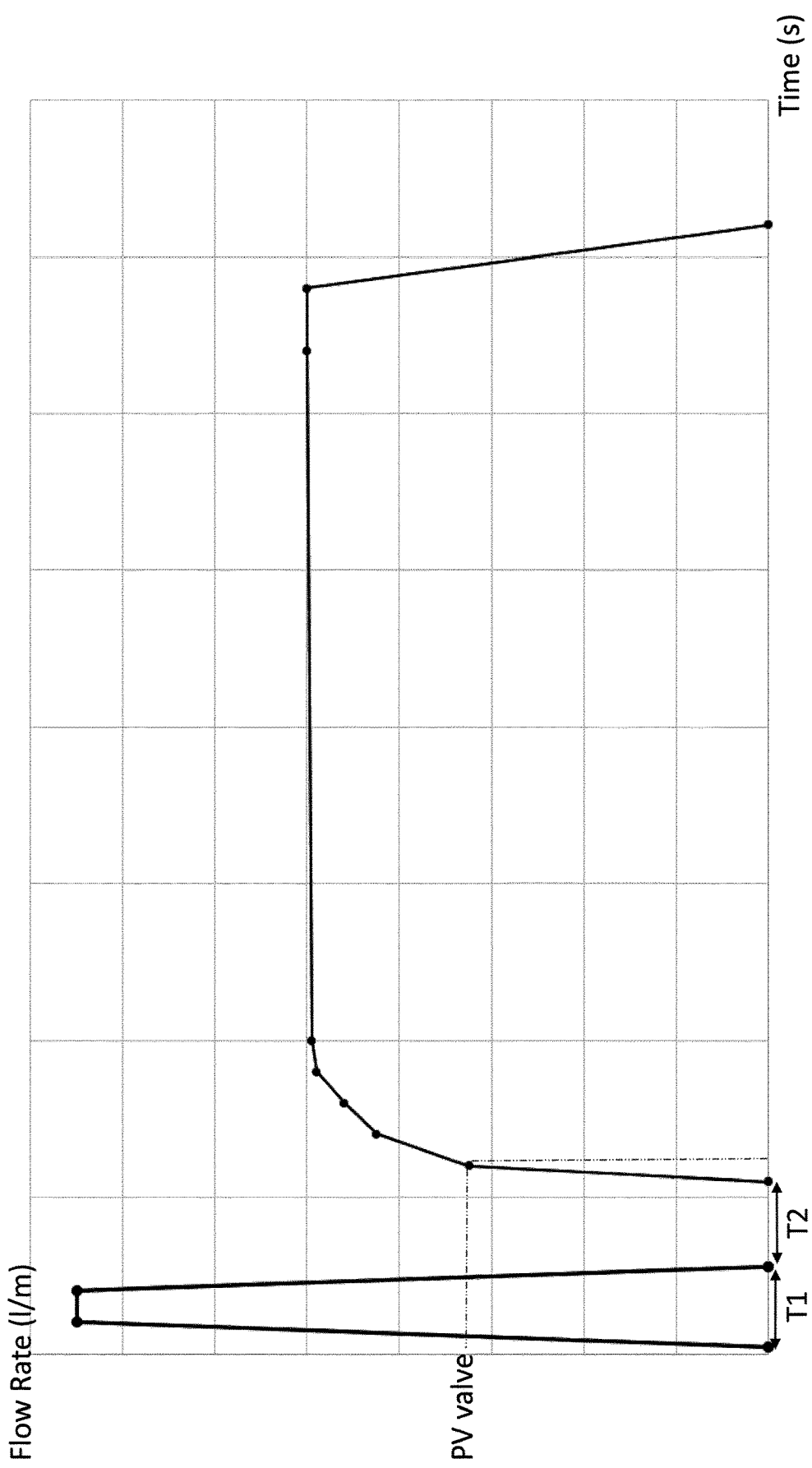
FIG. 11 is a graph of a first gas flow routine.

With reference to FIG. 11, a first gas flow routine is described. The liquid flow rate is zero throughout the first gas flow routine. A first time period T1 corresponds to the third time period T2 from the first gas and liquid flow routine (see FIG. 9). A second time period T2 has a zero gas flow rate. A third time period T3 corresponds to the sixth time period T8 from the first gas and liquid flow routine. The third time period T3 is substantially longer than the first time period T1 and the second time period T2. Apart from the differences noted, the first gas flow routine otherwise corresponds to the first gas and liquid flow routine.

Figure 12:
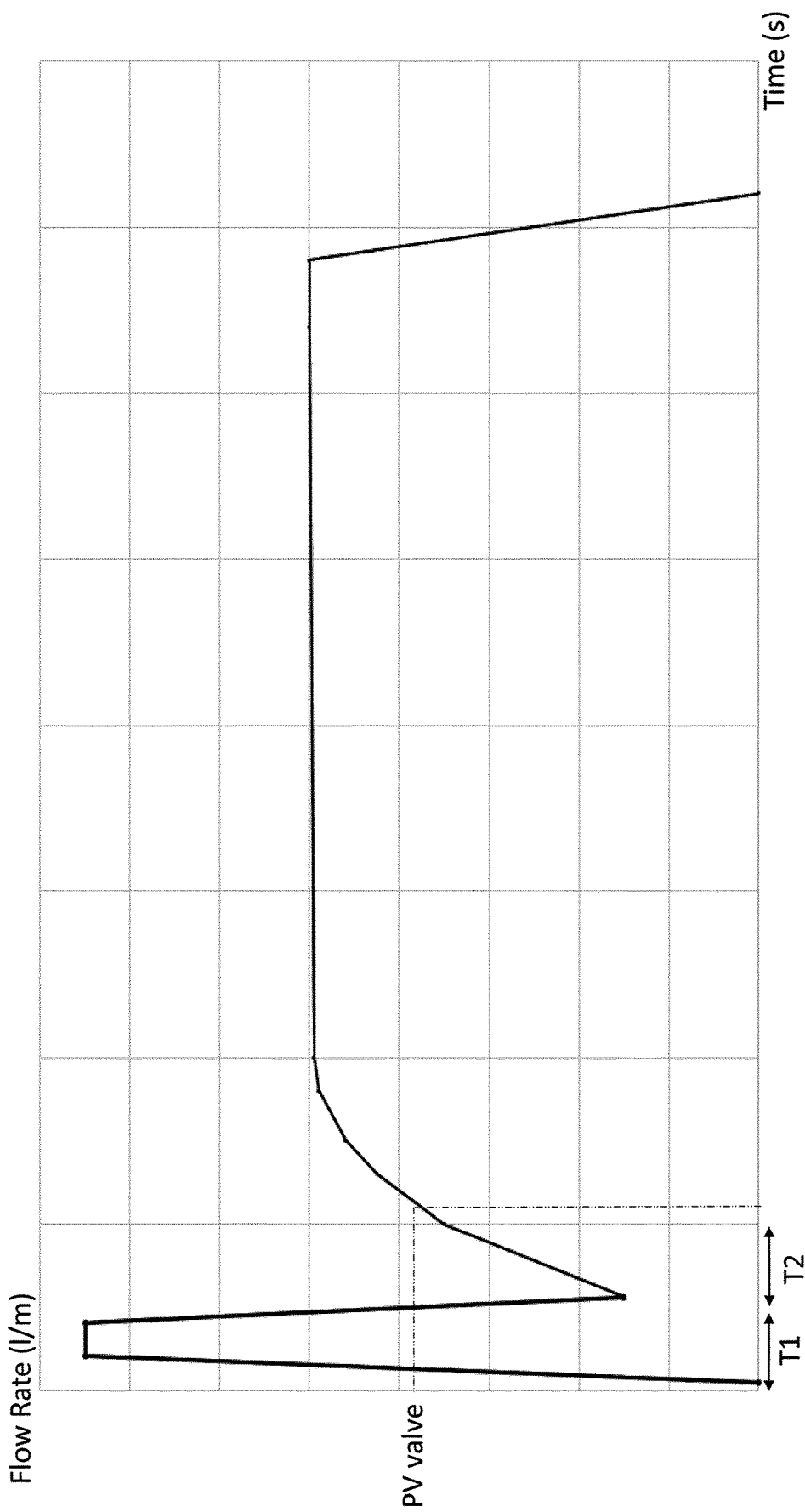
FIG. 12 is a graph of a second gas flow routine.

With reference to FIG. 12, a second gas flow routine is described. The second gas flow routine corresponds to the first gas flow routine, with the following differences. As with the difference between the first gas and liquid flow routine and the second gas and liquid flow routine, the second gas flow routine reduces the flow to a non-zero level. There is therefore no period of zero flow in the second gas flow routine corresponding to the second time period T2 in the first gas flow routine. Instead, a second time period T2 of the second gas flow routine corresponds to the third time period T3 of the first gas flow routine.

Although the routines described above are said to include periods of constant flow, in reality the flow rate will include slight variations during these constant flow periods, in particular due to the gas line variable valve having its position changed in response to measured changes in the pressure of the cavity 18.

A typical gas flow rate for the routines described above is less 1.2 litres per minute. A typical duration for any of the routines described above is between a few seconds and a few minutes. A short pulse of high flow rate is typically less than one second in duration. A pulse of liquid typically uses about 1 ml of liquid. The total amount of $CO_2$ used during a sequence is typically around 500 ml. These amounts are only guidelines and can vary significantly.

Figure 13:
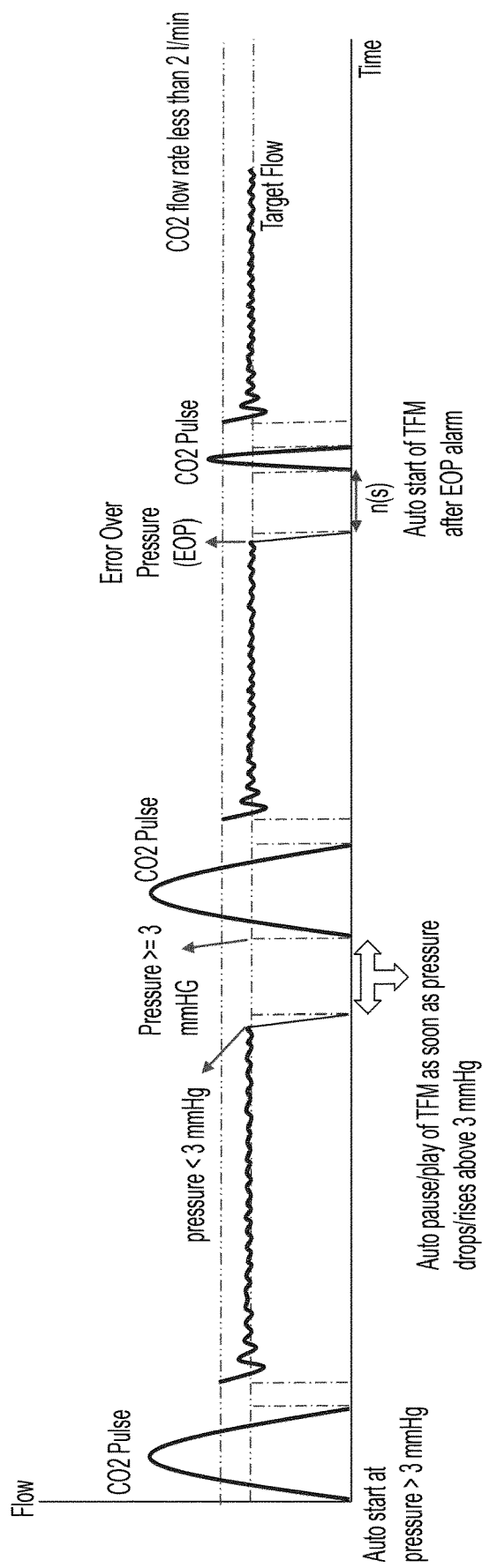
FIG. 13 is a graph of a further gas flow routine.

With reference to FIG. 13, the control unit 4 is configured to determine that the optical surface 16 of the scope 12 is inside or outside the cavity 18. The determination is based on a measurement from the pressure sensor. The pressure inside the cavity 18 is typically different from the pressure outside the cavity 18. The pressure sensor is configured to measure the pressure at the gas line gas output 40. While the channel device 8 and the scope accessory 10 are connected to the control unit 4, the pressure at the gas line gas output 40 will correspond to the pressure at the scope end of the gas line 58, i.e. the pressure adjacent the optical surface of the scope 12. In other embodiments, the pressure sensor is located on the channel device 8, on the scope accessory 10, on the scope 12 or on the optical surface 16.

The control unit 4 is configured to respond to a change in pressure measured by the pressure sensor indicative of the optical surface 16 of the scope 12 transitioning from a location outside the cavity 18 to a location inside the cavity 18 by initiating one or more of the flow routines described above. This provides automatic operation of the gas and/or liquid flow in order to remove condensation (or debris/fluid contamination) from the optical surface 16 of the scope 12. The condensation will typically begin forming upon entry of the optical surface 16 of the scope 12 into the cavity 18. The automatic initiation of the flow routine in response to entry of the optical surface 16 into the cavity 18 ensures that the presence of condensation on the optical surface 16 will be minimised rapidly. This automatic operation means that the operator does not have to use the activator 6 in order to activate the flow of liquid and/or gas. This automatic initiation of gas and/or liquid flow from the control unit 4 corresponds to an automatic flow mode of operation of the control unit 4, which can be activated and deactivated by the operator of the control unit 4.

The control unit 4 is configured to respond to a change in pressure measured by the pressure sensor indicative of the optical surface 16 of the scope 12 transitioning from a location inside the cavity 18 to a location outside the cavity 18 by terminating any gas and/or liquid flow. The gas and/or liquid flow is terminated by terminating any flow through the gas line gas output 40 and/or the wash line gas output 42. This is achieved using one or more of the valves in the control unit 4 as described above.

FIG. 13 depicts a gas flow routine initiated upon entry of the optical surface 16 of the scope 12 into the cavity 18. The pressure sensor detects a pressure greater than atmospheric pressure (e.g. a pressure greater than 3 mmHg), and a gas flow routine is initiated in response to the detection. The gas flow is activated or deactivated according to the detected pressure level being below or above respective threshold levels. The control unit 4 is therefore configured to ensure that the pressure in the cavity 18 remains between the predetermined threshold levels. This helps to ensure that the pressure within the cavity 18 is within a range appropriate for the surgical procedure being carried out. The control unit 4 is configured to terminate the gas flow in response to a determination that the pressure in the cavity 18 is higher than a maximum pressure threshold for the cavity 18. The control unit 4 is configured to initiate the gas flow in response to a determination that the pressure in the cavity 18 is lower than a minimum pressure threshold for the cavity 18. Upon initiation of the gas flow, the flow routine is initiated from the starting point of the respective flow routine. The control unit 4 is configured to enable the operator to set the value of the maximum pressure threshold based on a user input to the control unit 4. The control unit 4 is configured to enable the operator to set the value of the minimum pressure threshold based on a user input to the control unit 4. In some embodiments, the minimum pressure threshold is determined as a predetermined amount lower than the maximum pressure threshold. In some embodiments, there is only a maximum pressure threshold (and therefore no minimum pressure threshold).

In a typical use of the scope accessory 10 during a surgical procedure, the cavity 18 is insufflated by the insufflator 14 to a predetermined pressure level before the optical surface 16 of the scope 12 is inserted into the cavity 18. The control unit is configured to, in response to a detection indicative of the optical surface 16 entering the cavity 18 (e.g. a pressure increase), use an initial measurement of the pressure of the cavity 18 to determine the maximum pressure threshold for the cavity 18. In some embodiments, the maximum pressure threshold is set as a predetermined amount higher than the initial measurement of the pressure of the cavity 18 (e.g. 3 mmHg higher). The maximum pressure threshold is therefore set automatically without user involvement being required. The setting of the maximum pressure threshold as a predetermined amount higher than the initial measurement ensures that the gas flow from the control unit 4 into the cavity 18 does not immediately cause the maximum pressure threshold to be breached. In some embodiments, the control unit 4 calculates the initial measurement of the pressure of the cavity 18 by calculating an average of the pressure inside the cavity 18 for a predetermined period of time (e.g. 30 seconds). The control unit 4 is configured to display the pressure inside the cavity 18 on the cavity pressure display 50. The maximum pressure threshold is set as 3 mmHg higher than the measured value in order to show the working pressure in the cavity.

It will be understood that the above description of specific embodiments is by way of example only and is not intended to limit the scope of the present disclosure. Many modifications of the described embodiments, some of which are now described, are envisaged and intended to be within the scope of the present disclosure.

In some embodiments, the control panel is configured to implement several of the flow routines described above in sequence. The several flow routines may be implemented sequentially or with periods of zero flow in between. In some embodiments, the control panel is configured to implement one or more specific flow routines based on a determination of a type of the channel device connected to the control panel.

In some embodiments, the control panel is configured to prevent more than a threshold amount of gas and/or liquid passing through the scope accessory in a predetermined time period. In some embodiments, the predetermined time period is one minute. In some embodiments, once the threshold amount of gas and/or liquid has passed through the scope accessory, no further gas and/or liquid (as required) is passed through the scope accessory for the remainder of the predetermined time period.

In some embodiments, the control unit is the same device as the insufflator. The control unit and the insufflator are configured to use the same gas supply.

In some embodiments, the control unit is arranged differently than described above, for example with different panel arrangements, a WiFi connection rather than USB, and/or a touch-screen display instead of some or all of the buttons.

In some embodiments, the wash container is a wash cartridge. The wash cartridge is replaceable. In other embodiments, the wash container is not replaceable.

In some embodiments, the refill port of the valve is a double check valve. The double check valve allows fluid to be pushed in to the wash container but not back out again and also only allows the fluid to exit the wash container towards the scope accessory without return flow.

In some embodiments, the RFID transponder is located differently, for example on a different part of the gas line or on the wash line. In some embodiments, there is an RFID transponder on each of the gas line and the wash line. In some embodiments, an identification system other than RFID is used. An identifier of the channel device interacts with an identification sensor of the control panel in a similar manner as the RFID components described above. In some embodiments, the identifier of the channel device (which may be the RFID transponder) enables the control unit to determine parameters of the channel device and/or the scope accessory, for example a longitudinal length of the scope accessory, a usage history of the channel device and/or the scope accessory, and/or an indication of the origin of the channel device and/or the scope accessory, and/or an indication of the date of manufacture of the channel device and/or the scope accessory. In some embodiments, the control panel is configured to prevent operation of the assembly if the parameter(s) provided by the identifier of the channel device is/are of a predetermined type, for example if the date of manufacture is older than a predetermined threshold age, and/or if the usage history indicates that the channel device has been used before.

In some embodiments, the liquid and/or the gas are different from those described above. For example, the liquid may comprise surfactants or other cleaning agents. In some embodiments, the control panel is configured to store liquid and send the liquid down the wash line.

In some embodiments, the scope accessory is configured to fully surround the scope between the input end and the output end when the scope is within the scope accessory. In some embodiments, the conduit between the input end and the output end of the scope accessory is fully formed by the scope accessory. In some embodiments, the scope is integral with the scope assembly. In some embodiments, the scope is an endoscope, for example a flexible endoscope or a laparoscope, or another device with an optical surface is used instead of the scope.

The invention claimed is:

1. A channel device for transporting gas and liquid between a control unit and a scope accessory, the channel device comprising a wash line and a gas line, the wash line comprising:
    a wash line gas channel;
    a wash container;
    a piston; and
    a wash line wash channel,
    the wash line gas channel being configured to receive a gas from a wash line gas output of the control unit, the piston being configured to be actuated due to an increase in pressure in the wash line gas channel caused by the received gas to cause a liquid to be expelled from the wash container, the wash line wash channel being configured to transport the expelled liquid to the scope accessory,
    the wash line further comprising a valve configured to enable the liquid in the wash container to be replenished while the wash container remains in position in the wash line, the wash container being attached to the valve, the valve comprising an input port for receiving liquid from the wash container, an output port for transmitting liquid from the wash container towards the scope accessory, and a refill port to enable the liquid in the wash container to be replenished; and the gas line comprising a gas line channel configured to receive a gas from a gas line gas output of the control unit, and to transport the received gas to the scope accessory.

2. The channel device of claim 1, the wash container being replaceable in the wash line with a replacement wash container to provide a replacement supply of the liquid.

3. The channel device of claim 1, the channel device comprising an RFID transponder configured to enable the control unit to identify the channel device while the channel device is connected to the control unit.

4. The channel device of claim 1, wherein the scope accessory is arranged to guide the gas and/or liquid across an optical surface of a scope.

5. The channel device of claim 4, wherein the scope accessory comprises a conduit configured to transport the gas and/or the liquid from an input end of the scope accessory to an output end of the scope accessory.

6. The channel device of claim 1, the scope accessory being configured to removably receive a scope.

7. The channel device of claim 1, wherein the valve is a three way stopcock.

\* \* \* \* \*